(12) United States Patent
Casey, II et al.

(10) Patent No.: US 7,883,490 B2
(45) Date of Patent: Feb. 8, 2011

(54) MIXING AND DELIVERY OF THERAPEUTIC COMPOSITIONS

(75) Inventors: Thomas V. Casey, II, Grafton, MA (US); Bud Damiano, Westminster, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1007 days.

(21) Appl. No.: 10/278,248

(22) Filed: Oct. 23, 2002

(65) Prior Publication Data
US 2004/0092883 A1 May 13, 2004

(51) Int. Cl.
*A61M 37/00* (2006.01)
*A61M 5/00* (2006.01)

(52) U.S. Cl. .............. 604/82; 604/187; 604/87

(58) Field of Classification Search .......... 604/82, 604/83, 87, 88, 89, 90, 91, 92, 181, 187, 604/232, 416
See application file for complete search history.

(56) References Cited

U.S. PATENT DOCUMENTS

| | | |
|---|---|---|
| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,254,768 A * | 3/1981 | Ty ............................. 604/518 |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |

(Continued)

FOREIGN PATENT DOCUMENTS

AU    A-76186/98    10/1998

(Continued)

OTHER PUBLICATIONS

Cambridge Dictionaries Online (http://dictionary.cambridge.org/define.asp?key=59302&dict=CALD).*

(Continued)

*Primary Examiner*—Kevin C Sirmons
*Assistant Examiner*—Catherine N Witczak
(74) *Attorney, Agent, or Firm*—Seager, Tufte & Wickhem, LLC

(57) ABSTRACT

Syringe systems for mixing and delivery of particles into the body are disclosed. In some embodiments, a mixing and delivery medical syringe system can include a barrel including first and second detachable sections, and first and second compartments communicable through a conduit.

9 Claims, 8 Drawing Sheets

U.S. PATENT DOCUMENTS

| | | | |
|---|---|---|---|
| 4,412,836 A * | 11/1983 | Brignola | 604/87 |
| 4,413,070 A | 11/1983 | Rembaum | |
| 4,427,794 A | 1/1984 | Lange et al. | |
| 4,428,869 A | 1/1984 | Munteanu et al. | |
| 4,429,062 A | 1/1984 | Pasztor et al. | |
| 4,437,858 A * | 3/1984 | Ty | 604/90 |
| 4,442,843 A | 4/1984 | Rasor et al. | |
| 4,444,961 A | 4/1984 | Timm | |
| 4,452,773 A | 6/1984 | Molday | |
| 4,453,934 A | 6/1984 | Gahwiler et al. | |
| 4,456,693 A | 6/1984 | Welsh | |
| 4,459,145 A | 7/1984 | Elsholz | |
| 4,472,552 A | 9/1984 | Blouin | |
| 4,477,255 A | 10/1984 | Pasztor et al. | |
| 4,492,720 A | 1/1985 | Mosier | |
| 4,522,953 A | 6/1985 | Barby et al. | |
| 4,542,178 A | 9/1985 | Zimmermann et al. | |
| 4,551,132 A | 11/1985 | Pasztor et al. | |
| 4,551,436 A | 11/1985 | Johnson et al. | |
| 4,573,967 A | 3/1986 | Hargrove et al. | |
| 4,597,505 A * | 7/1986 | Mozley et al. | 220/89.2 |
| 4,622,362 A | 11/1986 | Rembaum | |
| 4,623,706 A | 11/1986 | Timm et al. | |
| 4,640,807 A | 2/1987 | Afghan et al. | |
| 4,657,756 A | 4/1987 | Rasor et al. | |
| 4,661,137 A | 4/1987 | Garnier et al. | |
| 4,663,358 A | 5/1987 | Hyon et al. | |
| 4,671,954 A | 6/1987 | Goldberg et al. | |
| 4,674,480 A | 6/1987 | Lemelson | |
| 4,675,113 A | 6/1987 | Graves et al. | |
| 4,678,710 A | 7/1987 | Sakimoto et al. | |
| 4,678,814 A | 7/1987 | Rembaum | |
| 4,680,320 A | 7/1987 | Uku et al. | |
| 4,681,119 A | 7/1987 | Rasor et al. | |
| 4,695,466 A | 9/1987 | Morishita et al. | |
| 4,713,076 A | 12/1987 | Draenert | |
| 4,742,086 A | 5/1988 | Masamizu et al. | |
| 4,743,507 A | 5/1988 | Franses et al. | |
| 4,772,635 A | 9/1988 | Mitschker et al. | |
| 4,782,097 A | 11/1988 | Jain et al. | |
| 4,789,501 A | 12/1988 | Day et al. | |
| 4,793,980 A | 12/1988 | Torobin | |
| 4,795,741 A | 1/1989 | Leshchiner et al. | |
| 4,801,458 A | 1/1989 | Hidaka et al. | |
| 4,804,366 A | 2/1989 | Zdeb et al. | |
| 4,819,637 A | 4/1989 | Dormandy, Jr. et al. | |
| 4,822,535 A | 4/1989 | Ekman et al. | |
| 4,833,237 A | 5/1989 | Kawamura et al. | |
| 4,850,978 A | 7/1989 | Dudar et al. | |
| 4,859,711 A | 8/1989 | Jain et al. | |
| 4,863,972 A | 9/1989 | Itagaki et al. | |
| 4,897,255 A | 1/1990 | Fritzberg et al. | |
| 4,929,400 A | 5/1990 | Rembaum et al. | |
| 4,933,372 A | 6/1990 | Feibush et al. | |
| 4,935,009 A * | 6/1990 | Caldwell et al. | 604/507 |
| 4,946,899 A | 8/1990 | Kennedy et al. | |
| 4,954,399 A | 9/1990 | Tani et al. | |
| 4,981,625 A | 1/1991 | Rhim et al. | |
| 4,990,340 A | 2/1991 | Hidaka et al. | |
| 4,999,188 A | 3/1991 | Solodovnik et al. | |
| 5,007,940 A | 4/1991 | Berg | |
| 5,011,677 A | 4/1991 | Day et al. | |
| H0915 H | 5/1991 | Gibbs | |
| 5,015,423 A | 5/1991 | Eguchi et al. | |
| 5,032,117 A | 7/1991 | Motta | |
| 5,034,324 A | 7/1991 | Shinozaki et al. | |
| 5,047,438 A | 9/1991 | Feibush et al. | |
| 5,079,274 A | 1/1992 | Schneider et al. | |
| 5,091,205 A | 2/1992 | Fan | |
| 5,106,903 A | 4/1992 | Vanderhoff et al. | |
| 5,114,421 A | 5/1992 | Polak | |
| 5,116,387 A | 5/1992 | Berg | |
| 5,120,349 A | 6/1992 | Stewart et al. | |
| 5,125,892 A | 6/1992 | Drudik | |
| 5,147,631 A | 9/1992 | Glajch et al. | |
| 5,147,937 A | 9/1992 | Frazza et al. | |
| 5,149,543 A | 9/1992 | Cohen et al. | |
| 5,158,573 A | 10/1992 | Berg | |
| 5,171,214 A | 12/1992 | Kolber et al. | |
| 5,171,217 A | 12/1992 | March et al. | |
| 5,181,921 A | 1/1993 | Makita et al. | |
| 5,190,760 A | 3/1993 | Baker | |
| 5,190,766 A | 3/1993 | Ishihara | |
| 5,192,301 A | 3/1993 | Kamiya et al. | |
| 5,202,352 A | 4/1993 | Okada et al. | |
| 5,216,096 A | 6/1993 | Hattori et al. | |
| 5,253,991 A | 10/1993 | Yokota et al. | |
| 5,260,002 A | 11/1993 | Wang | |
| 5,262,176 A | 11/1993 | Palmacci et al. | |
| 5,263,992 A | 11/1993 | Guire | |
| 5,288,763 A | 2/1994 | Li et al. | |
| 5,292,814 A | 3/1994 | Bayer et al. | |
| 5,302,369 A | 4/1994 | Day et al. | |
| 5,314,974 A | 5/1994 | Ito et al. | |
| 5,316,774 A | 5/1994 | Eury et al. | |
| RE34,640 E | 6/1994 | Kennedy et al. | |
| 5,320,639 A | 6/1994 | Rudnick | |
| 5,328,936 A | 7/1994 | Leifholtz et al. | |
| 5,336,263 A | 8/1994 | Ersek et al. | |
| 5,344,452 A | 9/1994 | Lemperle | |
| 5,344,867 A | 9/1994 | Morgan et al. | |
| 5,354,290 A | 10/1994 | Gross | |
| 5,369,133 A | 11/1994 | Ihm et al. | |
| 5,369,163 A | 11/1994 | Chiou et al. | |
| 5,382,260 A | 1/1995 | Dormandy, Jr. et al. | |
| 5,384,124 A | 1/1995 | Courteille et al. | |
| 5,397,303 A | 3/1995 | Sancoff et al. | |
| 5,398,851 A | 3/1995 | Sancoff et al. | |
| 5,403,870 A | 4/1995 | Gross | |
| 5,409,125 A | 4/1995 | Kimber et al. | |
| 5,417,982 A | 5/1995 | Modi | |
| 5,431,174 A | 7/1995 | Knute | |
| 5,435,645 A | 7/1995 | Faccioli et al. | |
| 5,443,495 A | 8/1995 | Buscemi et al. | |
| 5,445,614 A * | 8/1995 | Haber et al. | 604/89 |
| 5,456,693 A | 10/1995 | Conston et al. | |
| 5,468,801 A | 11/1995 | Antonelli et al. | |
| 5,469,854 A | 11/1995 | Unger et al. | |
| 5,476,472 A | 12/1995 | Dormandy, Jr. et al. | |
| 5,484,584 A | 1/1996 | Wallace et al. | |
| 5,490,984 A | 2/1996 | Freed | |
| 5,494,682 A | 2/1996 | Cohen et al. | |
| 5,494,940 A | 2/1996 | Unger et al. | |
| 5,512,604 A | 4/1996 | Demopolis | |
| 5,514,090 A | 5/1996 | Kriesel et al. | |
| 5,525,334 A | 6/1996 | Ito et al. | |
| 5,534,589 A | 7/1996 | Hager et al. | |
| 5,541,031 A | 7/1996 | Yamashita et al. | |
| 5,542,935 A | 8/1996 | Unger et al. | |
| 5,553,741 A | 9/1996 | Sancoff et al. | |
| 5,556,391 A | 9/1996 | Cercone et al. | |
| 5,556,610 A | 9/1996 | Yan et al. | |
| 5,558,255 A | 9/1996 | Sancoff et al. | |
| 5,558,822 A | 9/1996 | Gitman et al. | |
| 5,558,856 A | 9/1996 | Klaveness et al. | |
| 5,559,266 A | 9/1996 | Klaveness et al. | |
| 5,566,729 A | 10/1996 | Grabenkort et al. | |
| 5,567,415 A | 10/1996 | Porter | |
| 5,569,193 A | 10/1996 | Hofstetter et al. | |
| 5,569,449 A | 10/1996 | Klaveness et al. | |
| 5,569,468 A | 10/1996 | Modi | |
| 5,571,182 A | 11/1996 | Ersek et al. | |
| 5,580,575 A | 12/1996 | Unger et al. | |
| 5,583,162 A | 12/1996 | Li et al. | |

| | | | | | | |
|---|---|---|---|---|---|---|
| 5,585,112 A | 12/1996 | Unger et al. | | 6,028,066 A | 2/2000 | Unger |
| 5,595,821 A | 1/1997 | Hager et al. | | 6,047,861 A | 4/2000 | Vidal et al. |
| 5,622,657 A | 4/1997 | Takada et al. | | 6,048,908 A | 4/2000 | Kitagawa |
| 5,624,685 A | 4/1997 | Takahashi et al. | | 6,051,247 A | 4/2000 | Hench et al. |
| 5,635,215 A | 6/1997 | Boschetti et al. | | 6,056,721 A | 5/2000 | Shulze |
| 5,637,087 A | 6/1997 | O'Neil et al. | | 6,056,844 A | 5/2000 | Guiles et al. |
| 5,639,710 A | 6/1997 | Lo et al. | | 6,059,766 A | 5/2000 | Greff |
| 5,648,095 A | 7/1997 | Illum et al. | | 6,063,068 A | 5/2000 | Fowles et al. |
| 5,648,100 A | 7/1997 | Boschetti et al. | | 6,071,495 A | 6/2000 | Unger et al. |
| 5,650,116 A | 7/1997 | Thompson | | 6,071,497 A | 6/2000 | Steiner et al. |
| 5,651,990 A | 7/1997 | Takada et al. | | 6,073,759 A | 6/2000 | Lamborne et al. |
| 5,653,922 A | 8/1997 | Li et al. | | 6,090,925 A | 7/2000 | Woiszwillo et al. |
| 5,657,756 A | 8/1997 | Vrba | | 6,096,344 A | 8/2000 | Liu et al. |
| 5,681,576 A | 10/1997 | Henry | | 6,099,064 A | 8/2000 | Lund |
| 5,695,480 A | 12/1997 | Evans et al. | | 6,099,864 A | 8/2000 | Morrison et al. |
| 5,695,740 A | 12/1997 | Porter | | 6,100,306 A | 8/2000 | Li et al. |
| 5,698,271 A | 12/1997 | Liberti et al. | | 6,139,963 A | 10/2000 | Fujii et al. |
| 5,701,899 A | 12/1997 | Porter | | 6,149,623 A | 11/2000 | Reynolds |
| 5,704,918 A * | 1/1998 | Higashikawa ............... 604/191 | | 6,160,084 A | 12/2000 | Langer et al. |
| 5,715,824 A | 2/1998 | Unger et al. | | 6,162,377 A | 12/2000 | Ghosh et al. |
| 5,716,981 A | 2/1998 | Hunter et al. | | 6,165,193 A | 12/2000 | Greene, Jr. et al. |
| 5,718,884 A | 2/1998 | Klaveness et al. | | 6,179,817 B1 | 1/2001 | Zhong |
| 5,723,269 A | 3/1998 | Akagi et al. | | 6,191,193 B1 | 2/2001 | Lee et al. |
| 5,725,534 A | 3/1998 | Rasmussen | | 6,214,331 B1 | 4/2001 | Vanderhoff et al. |
| 5,733,925 A | 3/1998 | Kunz et al. | | 6,214,384 B1 | 4/2001 | Pallado et al. |
| 5,741,331 A | 4/1998 | Pinchuk | | 6,224,630 B1 | 5/2001 | Bao et al. |
| 5,746,734 A | 5/1998 | Dormandy, Jr. et al. | | 6,224,794 B1 | 5/2001 | Amsden et al. |
| 5,752,974 A | 5/1998 | Rhee et al. | | 6,235,224 B1 | 5/2001 | Mathiowitz et al. |
| 5,756,127 A | 5/1998 | Grisoni et al. | | 6,238,403 B1 | 5/2001 | Greene, Jr. et al. |
| 5,760,097 A | 6/1998 | Li et al. | | 6,245,090 B1 | 6/2001 | Gilson et al. |
| 5,766,147 A | 6/1998 | Sancoff et al. | | 6,251,661 B1 | 6/2001 | Urabe et al. |
| 5,770,222 A | 6/1998 | Unger et al. | | 6,258,055 B1 * | 7/2001 | McCrory et al. ............... 604/60 |
| 5,779,668 A | 7/1998 | Grabenkort | | 6,258,338 B1 | 7/2001 | Gray |
| 5,785,642 A | 7/1998 | Wallace et al. | | 6,261,585 B1 | 7/2001 | Sefton et al. |
| 5,785,682 A | 7/1998 | Grabenkort | | 6,264,861 B1 | 7/2001 | Tavernier et al. |
| 5,792,478 A | 8/1998 | Lawin et al. | | 6,267,154 B1 | 7/2001 | Felicelli et al. |
| 5,795,562 A | 8/1998 | Klaveness et al. | | 6,268,053 B1 | 7/2001 | Woiszwillo et al. |
| 5,797,953 A | 8/1998 | Tekulve | | 6,277,392 B1 | 8/2001 | Klein |
| 5,807,323 A | 9/1998 | Kriesel et al. | | 6,280,457 B1 | 8/2001 | Wallace et al. |
| 5,813,411 A | 9/1998 | Van Bladel et al. | | 6,291,605 B1 | 9/2001 | Freeman et al. |
| 5,823,198 A | 10/1998 | Jones et al. | | 6,296,604 B1 | 10/2001 | Garibaldi et al. |
| 5,827,502 A | 10/1998 | Klaveness et al. | | 6,296,622 B1 | 10/2001 | Kurz et al. |
| 5,827,531 A | 10/1998 | Morrison et al. | | 6,296,632 B1 | 10/2001 | Luscher et al. |
| 5,830,178 A | 11/1998 | Jones et al. | | 6,306,418 B1 | 10/2001 | Bley |
| 5,833,361 A | 11/1998 | Funk | | 6,306,419 B1 | 10/2001 | Vachon et al. |
| 5,840,387 A | 11/1998 | Berlowitz-Tarrant et al. | | 6,306,425 B1 | 10/2001 | Tice et al. |
| 5,846,518 A | 12/1998 | Yan et al. | | 6,306,427 B1 | 10/2001 | Annonier et al. |
| 5,853,752 A | 12/1998 | Unger et al. | | 6,312,407 B1 | 11/2001 | Zadno-Azizi et al. |
| 5,855,615 A | 1/1999 | Bley et al. | | 6,312,942 B1 | 11/2001 | Plüss-Wenzinger et al. |
| 5,863,957 A | 1/1999 | Li et al. | | 6,315,709 B1 | 11/2001 | Garibaldi et al. |
| 5,876,372 A | 3/1999 | Grabenkort et al. | | 6,335,384 B1 | 1/2002 | Evans et al. |
| 5,877,224 A | 3/1999 | Brocchini et al. | | 6,344,182 B1 | 2/2002 | Sutton et al. |
| 5,885,216 A | 3/1999 | Evans, III et al. | | 6,355,275 B1 | 3/2002 | Klein |
| 5,885,547 A | 3/1999 | Gray | | 6,368,658 B1 | 4/2002 | Schwarz et al. |
| 5,888,546 A | 3/1999 | Ji et al. | | 6,379,373 B1 | 4/2002 | Sawhney et al. |
| 5,888,930 A * | 3/1999 | Smith et al. ............... 504/359 | | 6,388,043 B1 | 5/2002 | Langer et al. |
| 5,891,155 A | 4/1999 | Irie | | 6,394,965 B1 | 5/2002 | Klein |
| 5,894,022 A | 4/1999 | Ji et al. | | 6,423,332 B1 | 7/2002 | Huxel et al. |
| 5,895,398 A | 4/1999 | Wensel et al. | | 6,432,437 B1 | 8/2002 | Hubbard |
| 5,895,411 A | 4/1999 | Irie | | 6,436,112 B2 | 8/2002 | Wensel et al. |
| 5,899,877 A | 5/1999 | Leibitzki et al. | | 6,443,941 B1 | 9/2002 | Slepian et al. |
| 5,902,832 A | 5/1999 | Van Bladel et al. | | 6,458,296 B1 | 10/2002 | Heinzen et al. |
| 5,902,834 A | 5/1999 | Porrvik | | 6,476,069 B2 | 11/2002 | Krall et al. |
| 5,922,025 A | 7/1999 | Hubbard | | 6,495,155 B1 | 12/2002 | Tice et al. |
| 5,922,304 A | 7/1999 | Unger | | 6,544,503 B1 | 4/2003 | Vanderhoff et al. |
| 5,928,626 A | 7/1999 | Klaveness et al. | | 6,544,544 B2 | 4/2003 | Hunter et al. |
| 5,935,553 A | 8/1999 | Unger et al. | | 6,545,097 B2 | 4/2003 | Pinchuk et al. |
| 5,951,160 A | 9/1999 | Ronk | | 6,575,896 B2 | 6/2003 | Silverman et al. |
| 5,957,848 A | 9/1999 | Sutton et al. | | 6,602,261 B2 | 8/2003 | Greene, Jr. et al. |
| 5,959,073 A | 9/1999 | Schlameus et al. | | 6,602,524 B2 | 8/2003 | Batich et al. |
| 6,003,566 A | 12/1999 | Thibault et al. | | 6,605,111 B2 | 8/2003 | Bose et al. |
| 6,015,546 A | 1/2000 | Sutton et al. | | 6,629,947 B1 | 10/2003 | Sahatjian et al. |
| 6,027,472 A * | 2/2000 | Kriesel et al. ............... 604/89 | | 6,632,531 B2 | 10/2003 | Blankenship |

| | | | | | | |
|---|---|---|---|---|---|---|
| 6,652,883 | B2 | 11/2003 | Goupil et al. | JP | 59-196738 | 11/1984 |
| 6,673,050 | B1 | 1/2004 | Farris | JP | 62-45637 | 2/1987 |
| 6,676,971 | B2 * | 1/2004 | Goupil et al. ............... 424/489 | JP | 4-74117 | 3/1992 |
| 6,680,046 | B1 | 1/2004 | Boschetti | JP | 6-57012 | 3/1994 |
| 6,692,515 | B2 * | 2/2004 | Boehm et al. ............... 606/213 | JP | 9-110678 | 4/1997 |
| 6,699,222 | B1 | 3/2004 | Jones et al. | JP | 9-165328 | 6/1997 |
| 6,723,067 | B2 * | 4/2004 | Nielson ..................... 604/82 | JP | 9-316271 | 12/1997 |
| 6,764,463 | B1 | 7/2004 | Farris | JP | 10-130329 | 5/1998 |
| 7,131,997 | B2 * | 11/2006 | Bourne et al. ............ 623/23.72 | JP | 2000189511 | 7/2000 |
| 7,449,236 | B2 * | 11/2008 | Lanphere et al. ............ 428/402 | JP | 2001079011 | 3/2001 |
| 7,462,366 | B2 * | 12/2008 | Lanphere et al. ............ 424/489 | JP | 2002 017848 | 1/2002 |
| 7,588,780 | B2 * | 9/2009 | Buiser et al. ............... 424/501 | NZ | 255409 | 2/1997 |
| 7,611,542 | B2 * | 11/2009 | Bourne et al. ............ 623/23.72 | NZ | 517377 | 8/2003 |
| 2001/0001835 | A1 | 5/2001 | Greene, Jr. et al. | TW | 421658 | 2/2001 |
| 2001/0016210 | A1 | 8/2001 | Mathiowitz et al. | WO | WO 91/12823 | 5/1991 |
| 2001/0036451 | A1 * | 11/2001 | Goupil et al. ............ 424/78.38 | WO | WO 92/21327 | 12/1992 |
| 2001/0051670 | A1 | 12/2001 | Goupil et al. | WO | WO 93/00063 | 1/1993 |
| 2002/0054912 | A1 | 5/2002 | Kim et al. | WO | WO 93/19702 | 10/1993 |
| 2002/0061954 | A1 | 5/2002 | Davis et al. | WO | WO 94/10936 | 5/1994 |
| 2002/0111580 | A1 * | 8/2002 | Richeal et al. ................. 604/89 | WO | WO 95/03036 | 2/1995 |
| 2002/0160109 | A1 | 10/2002 | Yeo et al. | WO | WO 95/22318 | 8/1995 |
| 2002/0182190 | A1 | 12/2002 | Naimark et al. | WO | WO 95/33553 | 12/1995 |
| 2002/0197208 | A1 | 12/2002 | Ruys et al. | WO | WO 96/37165 | 11/1996 |
| 2003/0007928 | A1 | 1/2003 | Gray | WO | WO 96/39464 | 12/1996 |
| 2003/0032935 | A1 * | 2/2003 | Damiano et al. ............. 604/403 | WO | WO 98/04616 | 2/1998 |
| 2003/0108614 | A1 | 6/2003 | Volkonsky et al. | WO | WO 98/10798 | 3/1998 |
| 2003/0183962 | A1 | 10/2003 | Buiser et al. | WO | WO 98/26737 | 6/1998 |
| 2003/0185895 | A1 | 10/2003 | Lanphere et al. | WO | WO98/47532 | 10/1998 |
| 2003/0185896 | A1 | 10/2003 | Buiser et al. | WO | WO 99/00187 | 1/1999 |
| 2003/0187320 | A1 | 10/2003 | Freyman | WO | WO 99/43380 | 2/1999 |
| 2003/0194390 | A1 | 10/2003 | Krall et al. | WO | WO 99/12577 | 3/1999 |
| 2003/0203985 | A1 | 10/2003 | Baldwin et al. | WO | WO 99/51278 | 10/1999 |
| 2003/0206864 | A1 | 11/2003 | Mangin | WO | WO 99/57176 | 11/1999 |
| 2003/0215519 | A1 | 11/2003 | Schwarz et al. | WO | WO 00/23054 | 4/2000 |
| 2003/0233150 | A1 | 12/2003 | Bourne et al. | WO | WO 00/32112 | 6/2000 |
| 2004/0076582 | A1 | 4/2004 | DiMatteo et al. | WO | WO 00/40259 | 7/2000 |
| 2004/0096662 | A1 | 5/2004 | Lanphere et al. | WO | WO 00/71196 A1 | 11/2000 |
| 2004/0101564 | A1 | 5/2004 | Rioux et al. | WO | WO 00/74633 | 12/2000 |
| 2004/0186377 | A1 | 9/2004 | Zhong et al. | WO | WO 01/12359 | 2/2001 |
| 2005/0025800 | A1 | 2/2005 | Tan | WO | WO 01/66016 | 9/2001 |
| 2005/0037047 | A1 | 2/2005 | Song | WO | WO 01/70291 A2 | 9/2001 |
| | | | | WO | WO 01/72281 | 10/2001 |
| | | | | WO | WO 01/76845 | 10/2001 |

FOREIGN PATENT DOCUMENTS

| | | |
|---|---|---|
| DE | 3 834 705 | 4/1990 |
| DE | 9414868.6 | 2/1995 |
| DE | 297 24 255 U1 | 10/2000 |
| DE | 100 26 620 | 3/2002 |
| EP | 0 067 459 A1 | 12/1982 |
| EP | 0112574 | 12/1983 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 A | 6/1994 |
| EP | 0 623 012 | 11/1994 |
| EP | 0 706 376 | 4/1996 |
| EP | 0 730 847 A1 | 9/1996 |
| EP | 0 744 940 | 12/1996 |
| EP | 0 797 988 | 10/1997 |
| EP | 0 067 459 | 3/1998 |
| EP | 0 764 047 | 8/2003 |
| EP | 0 993 337 | 4/2004 |
| ES | 2 096 521 | 3/1997 |
| FR | 1099362 | 9/1955 |
| GB | 743789 | 1/1956 |
| GB | 1130593 | 4/1966 |
| WO | WO 01/93920 | 12/2001 |
| WO | WO 02/11696 A2 | 2/2002 |
| WO | WO 02/34298 A1 | 5/2002 |
| WO | WO 02/34299 A1 | 5/2002 |
| WO | WO 02/34300 A1 | 5/2002 |
| WO | WO 02/43580 | 6/2002 |
| WO | WO 03/016364 | 2/2003 |
| WO | WO 03/051451 | 6/2003 |
| WO | WO03/082359 | 10/2003 |
| WO | WO 2004/019999 | 3/2004 |
| WO | WO 2004/073688 | 9/2004 |
| WO | WO 2004/075989 | 9/2004 |

OTHER PUBLICATIONS

Onelook.Com Dictionarly (http://onelook.com/?w=medicine&ls=a).*
Onelook.Com Dictionary (http://onelook.com/?w=powder&ls=a).*
Wikipedia entry; "Thrombin." http://en.wikipedia.org/wiki/thrombin.*
Wikipedia entry; "Fibrin." http://en.wikipedia.org/wiki/fibirinogen.*
Wikipedia entry; "Coagulation." http://en.wikipedia.org/wiki/coagulation.*
Wikipedia entry; "embolism." http://en.wikipedia.org/wiki/embolism.*
Yusi et al., "submuscosal Injection of Polyvinyl Alcohol in Artificially Created Vesico-Ureteral Reflux: A Preliminary Report," Asian J. Surg. 18(2): 122-127 (Apr. 1995).

Markus, H.S., "Experimental Aspects of High-Intensity Transient Signals in the Detection of Emboli," *J Clin Ultrasound* 23:81-87 (1995).

Schwarz, K.Q., "The Acoustic Filter: An Ultrasonic Blood Filter for the Heart-Lung Machine," *Journal of Thoracic and Cardiovascular Surgery* 104(6):1647-1653 (1992).

Barton, P. et al., "Embolization of Bone Metastases", *Journal of Vascular and Interventional Radiology*, vol. 7, No. 1, Jan.-Feb. 1996, p. 81-88.

Jiaqi, Y. et al., "A New Embolic Material: Super Absorbent Polymer (SAP) Microsphere and Its Embolic Effects", *Nippon Acta Radiologica* 1996 (56):19-24.

Mavligit, G. et al., "Gastrointestinal Leiomyosarcoma Metastatic to the Liver", *Cancer*, vol. 75, No. 8, Apr. 15, 1995, pp. 2083-2088.

Repa, I. et al., "Mortalities Associated with Use of a Commercial Suspension of Polyvinyl Alcohol", *Radiology* 1989; 170:395-399.

Rump, A. et al., "Pharmacokinetics of Intraarterial Mitomycin C in the Chemoembolisation Treatment of Liver Metastases", *Gen. Pharmac.* vol. 27, No. 4, pp. 669-671, 1996.

Thanoo, B. C. et al., "Preparation and Properties of Barium Sulphate and Methyl Iothalamate Tax Loaded Poly(vinyl Alcohol) Microspheres as Radiopaque Particulate Emboli", *Journal of Applied Biomaterials*, vol. 2, 67-72 (1991).

Zou, Ying-hua, et al. "Experimental Canine Hapatic Artery Embolization with Polyvinyl Alcohol Microspheres", *Zhong Hua Fang-She Xue ZaZhi*, Dec. 23, 1989 (6):330-332.

Zou, Ying-hua, et al. "Experimental Canine Hapatic Artery Embolization with Polyvinyl Alcohol Microspheres" (Translation), *Zhong Hua Fang-She Xue ZaZhi*, Dec. 23, 1989 (6):330-332.

PCT/US03/33674 Search Report dated Jun. 25, 2004.

Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.* 17:541-548, Mar. 1996.

Stridbeck, H. et al., "Collateral Circulation Following Repeated Distal Embolization of the Hepatic Artery in Pigs," *Invest Radiol* 1984;19:179-183.

Wright, K.C. et al., "Partial Splenic Embolization Using Polyvinyl Alcohol Foam, Dextran, Polystyrene, or Silicone," *Radiology* 142:351-354, Feb. 1982.

Kim et al., "Hollow Silica Spheres of Controlled Size and Porosity by Sol-Gel Processing," *J. Am. Ceram. Soc.*, 74(8):1987-1992 (Aug. 1991).

Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.

Barr, J.D., et al., "Polyvinyl Alcohol Foam Particles Sizes and Concentrations Injectable through Microcatheters", *JVIR*, vol. 9, No. 1, pp. 113-118; 1998.

Battinelli, L. et al., "New Class of Poly(vinyl alcohol) Polymrs as Column-Chromatography Stationary Phases for Candida Rugosa Lipase Isoforms Separation", *J. Chromatogr A*, vol. 753, No. 1, pp. 47-55; 1996.

Berenstein, A. et al., "Catheter and Material Selection for Transarterial Embolization: Technical Considerations. II. Materials.", *Radiology*, vol. 132, No. 3, pp. 631-639; 1979.

Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583, http://www.hepatitis-central.com/hcv/hcc/embolization/references.html.

Buhle, Jr. EL, "Re: Re: Hepatic Arterial Embolization", *UCLA Medicine Online*, Mar. 10, 1996, http://www.meds.com/archive/mol-cancer/1996/msg00128.html, 2 pages.

Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351-2356, 1996.

Burczak, et al., "Polymeric materials for biomedical purposes obtained by radiation methods. V. hybrid artificial pancreas", *Polim Med*, vol. 24, No. 1-2, pp. 45-55, 1994 (Entire document included—only Summary is in English).

Choe, et al., "An experimental study of embolic effect according to infusion rate and concentration of suspension in transarterial particulate embolization", *Invest Radiol*, vol. 32, No. 5, pp. 260-270, 1997.

Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25, Oct. 1982.

Clarian Health Methodist—Indiana Lions Gamma Knife Center, "Arteriovenous Malformation," http://www.clarian.com/tyhealth/gammaknife/cond_arter.asp, 4 pages, Last Updated on Mar. 20, 2000.

Colombo M, "Treatment of Hepatocellular Carcinoma", *Journal of Viral Hepatitis*, 4(Suppl. 1):125-130 (1997), http://home.texoma.net/~moreland/stats/hcc-9.html.

Derdeyn, et al., "Collagen-coated acrylic microspheres for embolotherapy: in vivo and in vitro characteristics", *American Journal of Neuroradiology*, vol. 18, No. 4, pp. 647-653, 1997.

Derdeyn, et al., "Polyvinyl alcohol particle size and suspension characteristics", *American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, vol. 83, No. 1, pp. 104-106, Jan. 1994.

"Fibroid Treatment Collective—Fibroid Embolization," 2 pages, http://www.fibroids.org.

Gander, et al., "Effect of polymeric network structure on drug release from cross-linked poly(vinyl alcohol) micromatrices", *Pharm Res*, vol. 6, No. 74, pp. 578-584, 1989.

Germano, et al., "Histopathological follow-up study of 66 cerebral arteriovenous malformations after therapeutic embolization with polyvinyl alcohol", *J Neurosurg*, vol. 76, No. 4, pp. 607-614, 1992.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, vol. 11, No. 10, pp. 1244-1255, Dec. 2000.

Gohel, et al., "Formulation design and optimization of modified-release microspheres of diclofenac sodium", *Drug Dev Ind Pharm*, vol. 25, No. 2, pp. 247-251, 1999.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992.

Horak et al., "Hydrogels in endovascular embolization. I. Spherical particles of poly (2-hydroxyethyl methacrylate) and their medicobiological properties", *Biomaterials*, 7(3):188-192 (May 1986).

Horak et al., "Hydrogels in endovascular embolization. II. Clinical use of spherical particles", *Biomaterials*, 7(6):467-470 (Nov. 1986).

Huang, et al., "Percutaneous endovascular embolization of intracerebral arteriovenous malformations. Experience in 72 cases", *Chin Med J*, vol. 108, No. 6, pp. 413-419, 1995.

Kai, et al., "The utility of the microcrystalline cellulose sphere as a particulate embolic agent: an experimental study", *American Journal of Radiology*, vol. 21, No. 6, pp. 1160-1163, 2000.

Kan, et al., "In vivo microscopy of the liver after injection of lipiodol into the hepatic artery and portal vein in the rat", *Acta Radiologica*, vol. 30, pp. 419-425, 1989.

Kerber et al., "Polyvinyl Alcohol Foam: Prepackaged Emboli for Therapeutic Embolization", *American Journal Roentgenol*, vol. 130, pp. 1193-1194, Jun. 1978.

Kerber, "Flow-Controlled Therapeutic Embolization: A Physiologic and Safe Technique", *AJR*, vol. 134, pp. 557-561, Mar. 1980.

Kim, et al., "Composite poly(vinyl alcohol) beads for controlled drug delivery", *Pharm Res*, vol. 9. No. 1, pp. 10-16, 1992.

Kurosaki et al., "Evaluation of PVA-Gel Spheres as GI-Transit Time Controlling Oral Drug Delivery System", *Proceedings of the 19th International Symposium on Controlled Release of Bioactive Materials*, Orlando, Florida, pp. 273-274, Jul. 26-31, 1992.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983 (Entire document included—only Abstract is in English).

Latchaw et al., "Polyvinyl Foam Embolization of Vascular and Neoplastic Lesions of the Head, Neck, and Spine", *Radiology*, vol. 131, pp. 669-679, Jun. 1979.

Leung et al., "Determinants of Postembolization Syndrome after Hepatic Chemoembolization", *Journal of Vascular and Interventional Radiology*, vol. 12, No. 3, pp. 320-326, Mar. 2001.

Markoff, et al., "Uterine arteriovenous malformation successfully embolized with a liquid polymer, isobutyl 2-cyanoacrylate", *Am. J. Obstet. Gynecol.*, 155:659-660 (Sep. 1986).

Matsumaru, et al., "Embolic materials for endovascular treatment of cerebral lesions", *J Biomater Sci Polym Ed*, vol. 8, No. 7, pp. 555-569, 1997.

Mid-America Interventional Radiological Society, "New Treatment for Uterine Fibroids Avoids Surgery," http://www.mirs.org/fibroids.htm, 6 pages, Submitted in Oct. 1999.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997.

Nakstad, et al., "Embolization of intracranial arteriovenous malformations and fistulas with polyvinyl alcohol particles and platinum fibre coils", *Neuroradiology*, vol. 34, No. 4, pp. 348-351, 1992.

Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997.

Nikishin LF et al., "Interventional radiology in diffuse toxic goiter", *European Congress of Radiology*, Abstract 9041, 1999, http://www.ecr.org/conferences/ecr1999/sciprg/abs/p090041.htm, 7 pages.

Ophir, et al., "Ultrasonic backscatter from contrast producing collagen microspheres", *Ultrasonic Imaging*, vol. 2, pp. 67-77, 1980.

Parker, et al., "A particulate contrast agent with potential for ultrasound imaging of liver", *Ultrasound in Medicine and Biology*, vol. 13, No. 9, pp. 555-566, 1987.

Pesant A.C. et al., "Dural fistulas involving the cavernous sinus: Treatment by embolization—7 cases", *European Congress of Radiology*, Abstract 3-088, 1997, http://www.ecr.org/conferences/ecr1997/sciprg/abs/9703088p.htm, 1 page.

Pritchard, et al., "Poly(Vinyl Alcohol): Basic Properties and Uses", London, England: Gordon and Breach Science Publishers, pp. 95-97, 1970.

Pryor J. and Berenstein A., "Epistaxis (Nose-bleeds)," http://www.wehealny.org/inn/Radiology/nosebleeds.html, 1 page.

Purdy, et al., "Arteriovenous malformations of the brain: choosing embolic materials to enhance safety and ease of excision", *J Neurosurg*, vol. 77, No. 2, pp. 217-222, 1992.

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, vol. 12, No. 2, pp. 187-193, Feb. 2001.

Ramos, et al., "Tumor vascular signals in renal masses: detection with Doppler US", *Radiology*, vol. 168, No. 3, pp. 633-637, 1988.

Ravin, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (Entire document included—only Abstract is in English).

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (Entire document included—only Summary is in English).

Shafik, "Intraesophageal Polytef injection for the treatment of reflux esophagitis," *Surg. Endosc.*, 10:329-331 (1996).

Spickler, et al., "The MR appearance of endovascular embolic agents in vitro with clinical correlation", *Comput Med Imaging Graph*, vol. 14, No. 6, pp. 415-423, 1990.

Spies JB "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.

Strunk, et al., "Treatment of congenital coronary arteriovenous malformations with microparticle embolization", *Cathet Cardiovasc Diagn*, vol. 22, No. 2, pp. 133-136, 1991.

Swanson DA et al., "The role of embolization and nephrectomy in the treatment of metastatic renal carcinoma", *Urologic Clinics of North America*, 7(3):719-730, 1980. University of Pennsylvania Cancer Center—Oncolink, http://www.oncolink.upenn.edu/pdg_html/cites/00/00585.html.

Tabata et al., "Tumor accumulation of poly(vinyl alcohol) of different sizes after intravenous injection", *Journal of Controlled Release*, vol. 50, pp. 123-133, Jan. 2, 1998.

Tadavarthy et al., "Polyvinyl Alcohol (Ivalon)—A New Embolic Material", *The American Journal of Roentgenology Radium Therapy and Nuclear Medicine*, vol. 125, No. 3, pp. 609-616, Nov. 1975.

Tadavarthy et al., "Polyvinyl Alcohol (Ivalon) as an Embolizing Agent", *Seminars in Interventional Radiology*, vol. 1, No. 2, pp. 101-109, Jun. 1984.

Tao, et al., "Study of microspheres for embolization of hepatic artery", *Acta Pharmaceutica Sinica*, vol. 23, No. 1, pp. 55-60, 1988.

Tao, et al., "Study of microspheres for embolization of hepatic artery", (Translation) *Acta Pharmaceutica Sinica*, vol. 23, No. 1, pp. 55-60, 1988.

Terada, et al., "Preoperative embolization of meningiomas fed by ophthalmic branch arteries", *Surg Neurol*, vol. 45, No. 2, pp. 161-166, 1996.

Thanoo, et al., "Controlled release of oral drugs from cross-linked polyvinyl alcohol microspheres", *J Pharm Pharmacol*, vol. 45, No. 1, pp. 16-20, 1993.

Thanoo, et al., "Tantalum loaded silicone micropsheres as particulate emboli", *J Microencapsul*, vol. 8, No. 1, pp. 95-101, 1991.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976 (Entire document included—only Abstract is in English).

The Fibroid Embolization Center of the New York United Hospital Medical Center, "Fibroid Facts," http://www.uhmc.com/fibro2.htm, 9 pages.

The Vanderbilt-Ingram Cancer Center, "Kidney Cancer," http://www.mc.Vanderbilt.Edu/cancer/cancerinfo/kidney.html, 1 page, 2001.

Tikkakoski, et al., "Preoperative embolization in the management of neck paragangliomas", *Laryngoscope*, vol. 107, pp. 821-826, 1997.

Touho, et al., "Intravascular treatment of spinal arteriovenous malformations using a microcatheter—with special reference to serial xylocaine tests and intravascular pressure monitoring"*Surgical Neurology*, vol. 42, No. 2, pp. 148-156, 1994.

UCLA Radiological Sciences, "A summary of terms appearing in this text," http://www.radsci.ucla.edu:8000/aneurysm/terms.html, 1 page.

University Medical Center Suny Stony Brook, Department of Urology, "Variococele and its treatment," http://www.hsc.sunysb.edu/urology/male_inf...variocoele_and_its_treatment.html, 8 pages, Last Updated on Mar. 12, 2001.

Vivas S et al., "Arterioportal fistula and hemobilia in a patient with hepatic transplant", Gastroenterol Hepatol, 21(2):88-9, http://www.doyma.es/copiani/revistas/gastro/abstr/abs_p080.html, Feb. 1998 (Entire document included—Abstract is in English).

Vogel F, "Nonsurgical Management of Uterine Fibroids," http://www.holyname.org/brochure/fibroids.html, 5 pages.

Wakhloo, et al., "Extended preoperative polyvinyl alcohol microembolization of intracranial meningiomas: Assessment of two embolization techniques",*American Journal of Neuroradiology*, vol. 14, pp. 571-582, 1993.
Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.
Walsh RM et al., "Role of Angiography and Embolization for Acute Massive Upper Gastronintestinal Hemorrhage," *J. Gastrointest. Surg.*, 3:61-66 (1999).
Wikholm G et al., "Embolization of Cerebral Arteriovenous Malformations: Part I—Technique, Morphology, and Complications", *Neurosurgery*, 39(3):448-459 (Sep. 1996).
Worthington-Kirsch RL, "Interventionalists offer management option for uterine fibroids," *Diagnostic Imaging*, 21(3):47-49, Mar. 1999, http://www.dimag.com/references/9903wortrefs.html.
Worthington-Kirsch, et al., "Uterine arterial embolization for the management of leiomyomas: Quality-of-life assessment and clinical response", *Radiology*, vol. 208, No. 3, 625-629, 1998.
Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radiol.*, vol. 19, pp. 139-145, 1996.
Abbara et al., "Transcervical Expulsion of a Fibroid as a Result of Uterine Artery Embolization for Leiomyomata", *JVIR*, vol. 10, No. 4, pp. 409-411, 1999.
Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.
Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.
Ahuja, A.A., "Platinum Coil Coatings to Increase Thrombogenicity: A Preliminary Study in Rabbits", *AJNR Am. J. Neuroradiol.* 14:794-798; Jul./Aug. 1993.
Antibody Labeling, http://www.altcorp.com/AffinityLabeling/ablaeling.htm, pp. 1-6, May 20, 2003.
Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.
Bourke et al., "Protein Drug Release from Photocrosslinked Poly(vinyl alcohol) Hydrogels," *Society for Biomaterials 28th Annual Meeting Transactions*, p. 144 (2002).
Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.
Brockman, J. et al., "Radiolabeling of p-Bz-DOTA-CD-11c antibody with $^{88}$Y: Conjugation, Labeling, Biodistribution studies", 2 pages, 2000 http://www.kernchemie.uni-mainz.de/downloads/jb2000/b14_brockmann.pdf.
Capozza et al., "Endoscopic treatment of vesico-ureteric reflux and urinary incontinence: technical problems in the paediatric patient," *British Journal of Urology*, 75(4):538-542 (Apr. 1995).
Carroll, B.A. et al., "Microbubbles as Ultrasonic Contrast Agents", *Investigative Radiology*, vol. 14, No. 3, p. 374, Supplement to May-Jun. 1979.
Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.
Carstensen, E.L. et al., "Determination of the Acoustic Properties of Blood and its Components", *Journal of Acoustical Society of America*, vol. 25, No. 2, pp. 286-289, Mar. 1953.
Cirkel, U. et al., "Experience with Leuprorelin Acetate Depot in the Treatment of Fibroids: A German Multicentre Study", *Clinical Therapeutics*, vol. 14, Suppl. A, 1992.
Concentric Medical, Inc.- Product Information (3 pages), 2002.
Cruise et al., "In Vitro and In Vivo Characterization of a Hydrogel-Based Aneurysm Embolization System," *Society for Biomaterials 28th Annual Meeting Transactions*, p. 203 (2002).

Deasy, P. B., "*Microencapsulation and Related Drug Processes*", New York, NY, Marcel Dekker, Inc., 345 pages, 1984 (Table of Contents only).
DeGast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.
Duckwiler et al., "Catheters, embolic agents spark neurointervention," *Diagnostic Imaging*, 16(5):66-72 (May 1994).
Ersek et al., "Bioplastique: A New Textured Copolymer Microparticle Promises Permanence in Soft-Tissue Augmentation," *Plastic and Reconstructive Surgery*, 87(4):693-702 (Apr. 1991).
Eskridge, "Interventional Neuroradiology," *Radiology*, 172:991-1006 (Nov. 1989).
Feldman, L. et al., "Transcatheter Vessel Occlusion: Angiographic Results Versus Clinical Success", *Radiology*, vol. 147, pp. 1-5, Apr. 1983.
Ferrofluids, Physical Properties and Applications Ferrofluidics Corp., Nashua, NH, 5 pages, 1986.
FeRx Incorporated, FERX Profile http://www.biotechshares.com/FERX.htm, 4 pages (Retrieved from the internet on Jun. 26, 2003)
Fritzsch, T. et al., "SH U 508, A Transpulmonary Echocontrast Agent", *Investigative Radiology*, vol. 25, Supplement 1, pp. S160-S161, Sep. 1990.
Fujimoto, S. et al., "Biodegradable Mitomycin C Microspheres Given Intra-Arterially for Inoperable Hepatic Cancer", *Cancer*, vol. 56, pp. 2404-2410, 1985.
Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.
Goldberg, B.B., "Ultrasonic Cholangiography", *Radiology*, vol. 118, pp. 401-404, Feb. 1976.
Gramiak et al., "Echocirdiography of the Aortic Root," *Investigative Radiology*, 3(5):356-366 (Sep.-Oct. 1968).
Gramiak, R. et al., "Ultrasound Cardiography: Contrast Studies in Anatomy and Function", *Radiology*, vol. 92, No. 5, pp. 939-948, Apr. 1969.
Greenwood, L.H. et al., "Obstetric and Nonmalignant Gynecologic Bleeding: Treatment with Angiographic Embolization", *Radiology*, vol. 164, No. 1, pp. 155-159, Jul. 1987.
Gupta et al., "Plasma-induced graft polymerization of acrylic acid onto poly(ethylene terephthalate) films: characterization and human smooth muscle cell growth on grafted films," *Biomaterials*, 23:863-871 (2002).
Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).
Hirano et al., "Transcutaneous Intrafold Injection for Unilateral Vocal Fold Paralysis: Functional Results," *Ann. Otol. Rhinol Laryngol.*, 99(8):598-604 (Aug. 1990).
"Injectable Tissue Implant Could Repair Ravages of Surgery", Clemson University, *Biotech Week*, Oct. 22, 2003, p. 117.
Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.ion.org/Journals/pb.
Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).
Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.
Kerber, C., "Balloon Catheter with a Calibrated Leak", *Radiology*, vol. 120, pp. 547-550, Sep. 1976.
Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).
Kim et al., "Poly(vinyl alcohol) beads with core-shell structure for drug delivery," *Cosmetic and Pharmaceutical Applications of Polymers*, Plenum Press, New York, pp. 209-214 (1991).

Kim et al., "Suspension polymerized poly(vinyl alcohol) beads for drug delivery," *Polymeric Materials: Science and Engineering, Proceedings of the ACS Division of Polymeric Materials: Science and Engineering*, 63:64-67 (1990).

Kochan, J.P. et al., "Interventional Neuroradiology: Current Practices and Techniques at Temple University Hospital," http://www.temple.edu/radiology/stroke.html, 5 pages.

Krinick et al., "A polymeric drug delivery system for the simultaneous delivery of drugs activatable by enzymes and/or light," *J. Biomater. Sci. Polymer Edn*, 5(4):303-324 (1994).

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurbatova, G.T. et al., "Magnetically-guided Anesthetics Based on Highly Dispersed Iron Powders Coated by Polyacrylamide", Biofizika, vol. 47, No. 2, pp. 331-337, Mar.-Apr. 2002 http://intapp.medscape.com/px/medlineapp.

Laurent, "Materials and biomaterials for interventional radiology," *Biomed. & Pharmacother.*, 52:76-88 (1998).

Lemperle et al., "PMMA Microspheres for Intradermal Implantation: Part I. Animal Research," *Annals of Plastic Surgery*, 26(1):56-63 (Jan. 1991).

Lendlein, A. et al., "Biodegradable, Elastic Shape-Memory Polymers for Potential Biomedical Applications", *Science*, vol. 296, pp. 1673-1676, May 31, 2002.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Levy et al., "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7):15-20 (Jul. 2000).

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Maruhashi, "Modified Polyvinyl Alcohols I and II," *Polyvinyl Alcohol—Developments*, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.

Mather, P.T., Research Group Homepage, Basic Goals and Methods, http://www.ims.uconn.edu/~mather, 4 pages.

Matsumoto, H. et al., "Basic Fibroblast Growth Factor Released from a Platinum Coil with a Polyvinyl Alcohol Core Enhances Cellular Proliferation and Vascular Wall Thickness: An in Vitro and in Vivo Study", *Neurosurgery*, vol. 53, No. 2, pp. 402-408, Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

MerocelXL Sponge with Hytrol http://www.xomed.com/newproducts/merocelxl/merocelx1_earwick.asp, 3 pages, 2001.

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Particles", *Int. J Hyperthermia*, vol. 19, No. 1, pp. 23-24, Feb. 2003, http://www.tandf.co.uk/journals.

Namiki, "Application of Teflon Paste for Urinary Incontinence—Report of 2 Cases," *Uro. Int.*, 39:280-282 (1984).

Orienti et al., "Crosslinked Polyvinylalcohol Hydrogels as Vehicles for Hydrophilic Drugs," *Arch. Pharm. Pharm. Med. Chem.*, 333:421-424 (2000).

Orsini, L. F. et al., "Pelvic Organs in Premenarcheal Girls: Real-Time Ultrasonography", Radiology, vol. 153, No. 1, pp. 113-116, Oct. 1984.

Pedley et al., "Hydrogels in Biomedical Applications," *British Polymer Journal*, 12:99-110 (Sep. 1980).

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Pistel et al., "Brush-like branched biodegradable polyesters, part III Protein release from microspheres of poly(vinyl alcohol)-graft-poly($_{D,L}$-lactic-co-glycolic acid)," *Journal of Controlled Release*, 73:7-20 (2001).

Politano et al., "Periurethral Teflon Injection for Urinary Incontinence," *The Journal of Urology*, 111:180-183 (1974).

Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.

Progelhof et al., "Table 4.21. Properties of electrical insulating films (101)," *Polymer Engineering Principles: Properties. Processes. and Tests for Design, Hanser Publishers*, Munich, p. 383 (1993).

PVA Plus, AngioDynamics® Inc., "Reliable PVA Foam Formulated for Consistency and Controlled Delivery—Embolization Particles Ordering Information," www.angiodynamics.com, 2 pages (Aug. 2002).

Ravina, J.H. et al., "Advantage of Pre-Operative Embolization of Fibroids: About a Multicentric Set of 31 Cases", *Contracept. Fend. Sex.*, vol. 23, No. 1, pp. 45-49, Jan. 1995 (abstract).

Ravina, J.H. et al., "Arterial Embolisation to Treat Uterine Myomata", *Lancet*, vol. 346, pp. 671-674, Sep. 9, 1995.

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (Summary).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Schetky, "Shape-Memory Alloys," *Encyclopedia of Chemical Technology*, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Shafik, "Intraesophageal Polytef injection for the treatment of reflux esophagitis," *Surg. Endosc.*, 10:329-331 (1996).

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres (Yttrium-90 Microspheres), pp. 1-12.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," *J. Vasc. Interv. Radiol.*, 14:89-98 (2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=00047706-121F-1CD0-B4A8809EC588, 2 pages.

Smith et al., "Evaluation of Polydimethylsiloxane as an alternative in the Endoscopic Treatment of Vesicoureteral Reflux," *The Journal of Urology*, 152:1221-1224 (Oct. 1994).

Smith, M.D. et at, "Left Heart Opacification with Peripheral Venous Injection of a New Saccharide Echo Contrast Agent in Dogs", *JACC*, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976.

Tian et al., "Design and synthesis of amphiphilic poly (ethylene glycol) derivatives as micellar drug delivery systems," *Polymer Preprints*, 43(2):719-720 (Fall 2002).

Toon, "Improving a Key Weapon Against Cancer," Research Horizons, pp. 11-12, Spring/Summer 2001.

Waltman, A.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Winters et al., "Periurethral injection of collagen in the treatment of intrinsic sphincteric deficiency in the female patient," *The Urologic Clinics of North America*, 22(3):673-678 (Aug. 1995).

Wu, A.M., "Engineered Antibodies for Breast Cancer Imaging and Therapy," http://www.cbcrp.org/research/PageGrant.asp?grant_id=111, 3 pages, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Jack, Clifford R., Jr. et al., "Radiolabeled Polyvinyl Alcohol Particles: A Potential Agent to Monitor Embolization Procedures," Nuclear Medicine and Biology International Journal of Radiation Applications and Instrumentation Part B, vol. 13, No. 3 (1986) pp. 235-243.

Joy, Christopher, MD et al., "Use of Preoperative Embolization in the Treatment of Vascular Metastatic Lesions of the Spine," American Academy of Orthopaedic Surgeons 1991 Annual Meeting—Scientific Program, http://www.aaos.org/wordhtml/anmeet91/scipro/ppr472.htm, 1 sheet, printed on or before Oct. 23, 2002.

Kurata, Akira et al., "Preoperative Embolization for Meningiomas Using PVA Particles," Neurol. Surg. vol. 20, No. 4, (1992) pp. 367-373; abstract, tables and figure captions in English language.

Oregon Health Sciences University, Fibroid Embolization: http://www.uhmc.edu/dotter-fibroid, 34 sheets, printed on or before Oct. 23, 2002.

"Chapter 1—Common Disorders of the Reproductive System," PDR Family Guide to Women's Health, http://www.healthsquare.com/pdrfg/wh/chapters/wh1ch01.htm, 24 sheets, printed on or before Oct. 23, 2002.

"Fibroid Embolization," Fibroid Treatment Collective, 2 sheets, printed on or before Oct. 23, 2002 http://www.fibroids.com.

\* cited by examiner

FIG. 5A
FIG. 5B
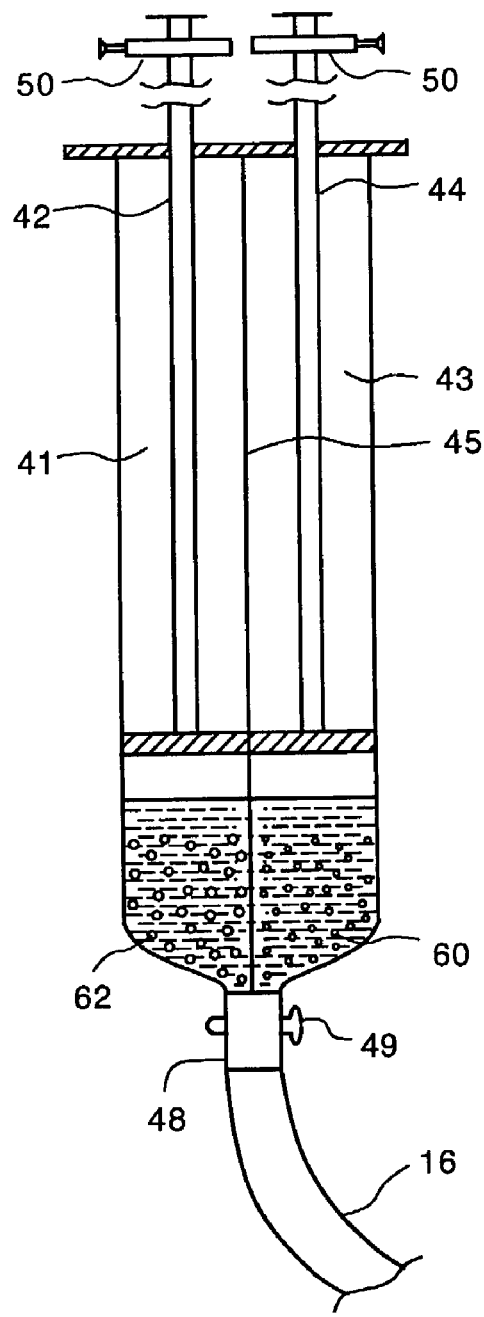
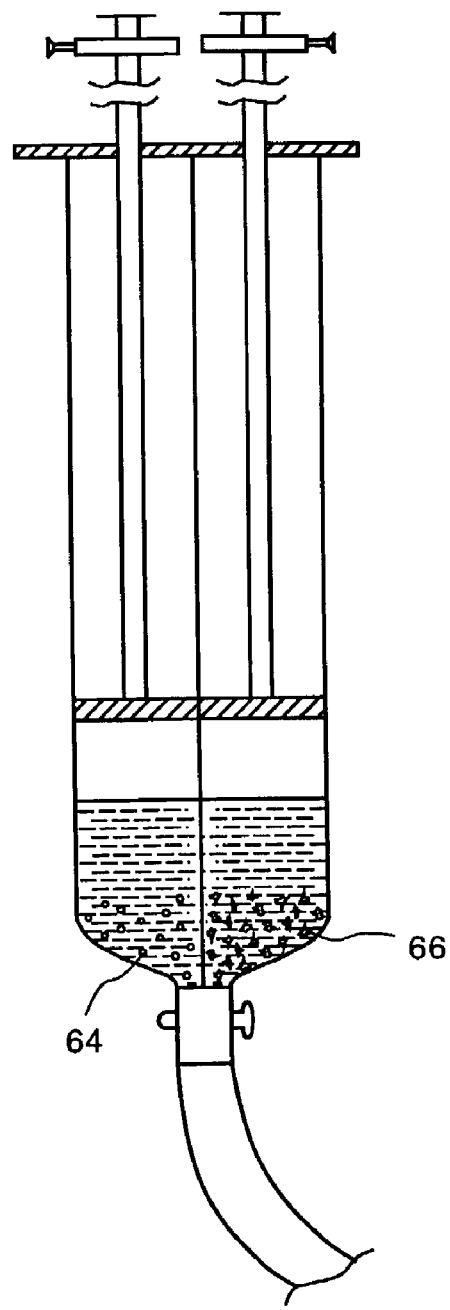

MIXING AND DELIVERY OF THERAPEUTIC COMPOSITIONS

TECHNICAL FIELD

This invention relates to mixing and delivery of therapeutic compositions.

BACKGROUND

Therapeutic vascular occlusions (embolizations) are induced by the introduction of various substances (embolic material, such as embolic particles) into a patient's circulatory system for the purpose of occluding vessels, either to arrest or to prevent hemorrhaging or to defunctionalize a structure or an organ. Typically, the components of an embolic composition-embolic particles in hydrating material (such as saline) and contrast agent (used for tracking the path of the embolic particles inside the body) are stored separately and mixed together at the time of injection into the body by the physician.

SUMMARY

In one aspect the invention features a mixing and delivery medical syringe system. The medical syringe system includes a barrel including first and second detachable sections, and first and second compartments communicable through a conduit.

In another aspect the invention feature a mixing and delivery medical syringe system. The medical syringe system includes a barrel having first and second compartments arranged in parallel along the barrel, the compartments communicable through a pressure-activated conduit.

In another aspect, the invention features a kit for medicant mixing and delivery, including a syringe system, which includes a barrel assembled from multiple sections, including a first section having a first chamber, and a second section having a second chamber. The syringe system includes a conduit between the first and second chambers through which flow can be controlled. The kit further includes a first container containing a first composition, and a second container containing a second composition.

In another aspect, the invention features a method for delivering injectable polymer particles by providing a syringe. The syringe includes a first compartment and a second compartment. A first component including injectable particles is loaded into at least one compartment, and the syringe is actuated to deliver the particles.

Embodiments can include one or more of the following. The conduit can include a pressure-activated separator. The separator can include a failure membrane. The failure membrane can include a weakened region. The weakened region preferentially effects rupture about a central region of the membrane. The weakened region preferentially affects rupture such that an attachment portion is not ruptured. The pressure-activated conduit can include a valve.

The first and the second compartments can be arranged serially along the syringe barrel. The barrel can include a vent valve. The barrel can include a fluid outlet and the outlet can include a valve. The first section can include the first chamber and the second section can include the second chamber. The conduit can be in one of the first or second sections.

The first composition can include injectable polymer particles. The particles can be embolic particles. The second composition can be a contrast agent. Alternatively, the second composition can include an anticancer agent.

The syringe can include a conduit between the compartments. A first component including injectable particles is loaded into at least one compartment and a second component is loaded into the second compartment. The first component and the second component are mixed in the syringe by flowing at least one of the components through the conduit. The second component can include a contrast agent. The second component can include a drug.

The method can include loading a second composition in the second compartment. The second composition can include polymer particles. The first component and second component can be delivered sequentially.

The first component and the second component can include polymer particles of different sizes or alternatively, of different shapes. The first component can include particles that are substantially spherical.

Embodiments may include one or more advantages. For example, pre-mixing the components may be undesirable because the shelf life of the mixed composition may be reduced for e.g., due to chemical interactions between a contrast agent and embolic particles.

The details of one or more embodiments of the invention are set forth in the accompanying drawings and the description below. Other features, aspects, and advantages of the invention will be apparent from the description and drawings, and from the claims.

DESCRIPTION OF DRAWINGS

FIG. 5A is a cross-sectional schematic of a syringe apparatus for mixing and delivery of particles of different sizes.

FIG. 5B is a cross-sectional schematic of a syringe apparatus for mixing and delivery of particles of different shapes.

Like reference symbols in the various drawings indicate like elements.

DETAILED DESCRIPTION

Figure 1A:
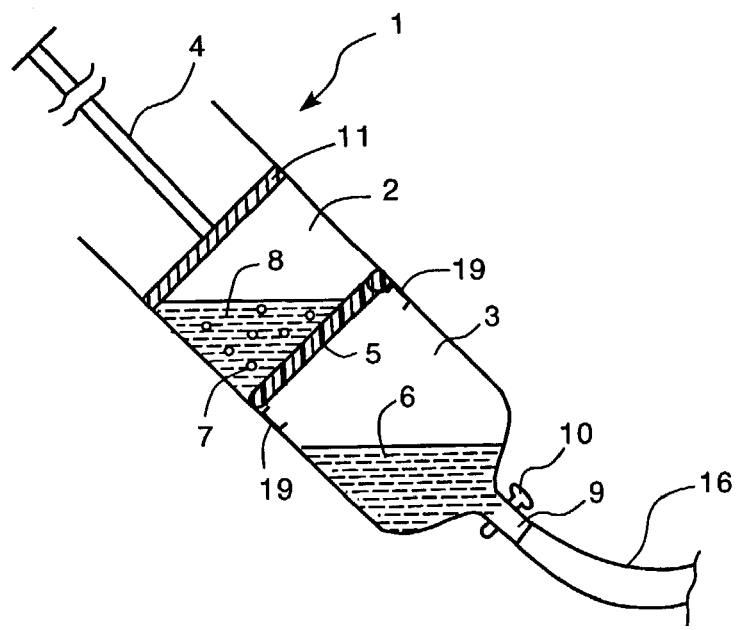
FIG. 1A is a cross-sectional schematic of a syringe apparatus for mixing and delivery of a composition into the body.

Referring to FIG. 1A, a syringe apparatus 1 includes a body with an upper compartment 2, a lower compartment 3, a plunger 4 with a plunger base 11, a membrane 5, and a connector 9, which could be a luer connector, fitted with a stopcock 10. The lower compartment 3 contains a contrast agent 6 and the upper compartment 2 contains a combination of particles such as embolic particles 7 and a hydrating fluid such as saline 8. The upper compartment 2 and lower compartment 3 are fitted together at junction 19. The membrane 5 can be made of a polymer material or of cellulose based materials, such as cellulose acetate, that provides a liquid-tight seal between the upper and lower compartments so that the contrast agent may be isolated from interaction with the embolic material and saline mixture until the time of injection into the body.

Figure 1B:
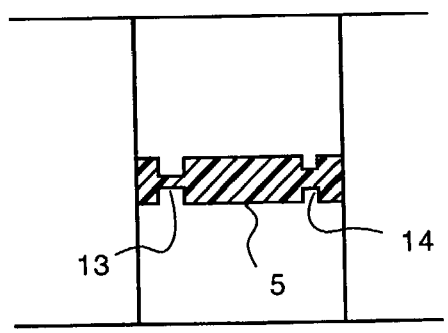
FIG. 1B is an enlarged cross-sectional view showing a failure membrane of the syringe of FIG. 1A.
Figure 1C:
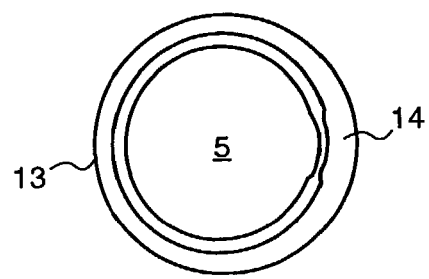
FIG. 1C is a top view of the failure membrane of the syringe of FIG. 1A.

Referring to FIGS. 1B and 1C, expanded views of the membrane 5 are illustrated. The membrane 5 has a failure region 13 and a hinge region 14. In one embodiment, the failure and hinge regions can be regions of reduced thickness. The thickness of the failure region 13 is less than the thickness of the hinge region 14 such that the membrane will fail preferentially at the failure region 13 and bend preferentially at the hinge region 14, in response to pressure increase in the upper compartment 2. Referring to FIG. 1C, a top view of the membrane 5 is illustrated showing the failure region 13 extending substantially around most of the circumference of the membrane, and the hinge region 14 extending along a short segment of the circumference. The reduced thickness regions of the membrane can be formed by heating, scoring or laser ablation.

Figure 1D:
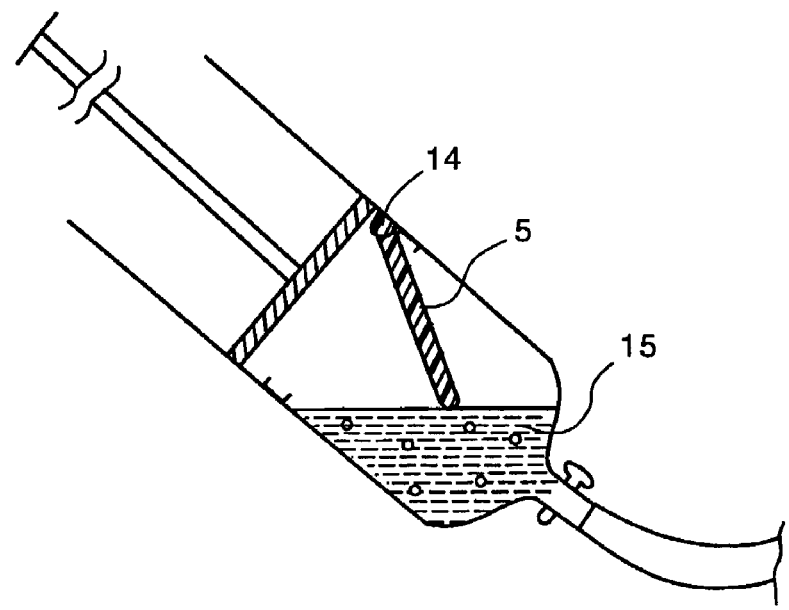
FIG. 1D illustrates mixing of the components using the syringe of FIG. 1A.

Referring to FIG. 1D, with the stopcock 10 closed, pressure is applied in the upper compartment by depressing the plunger. The applied pressure on the failure membrane 5 causes it to rupture at the failure region 13 and to bend at the hinge region 14. The embolic particles and saline in the upper compartment 2 travel to the lower compartment 3 and mix with the contrast agent to form the mixed embolic composition 15. Because the embolic particles are initially located in the upper compartment and the contrast in the lower compartment, the particles fall into the contrast solution in a turbulent manner which enhances mixing and the creation of a uniform suspension of the particles in the mixture.

Figure 1E:
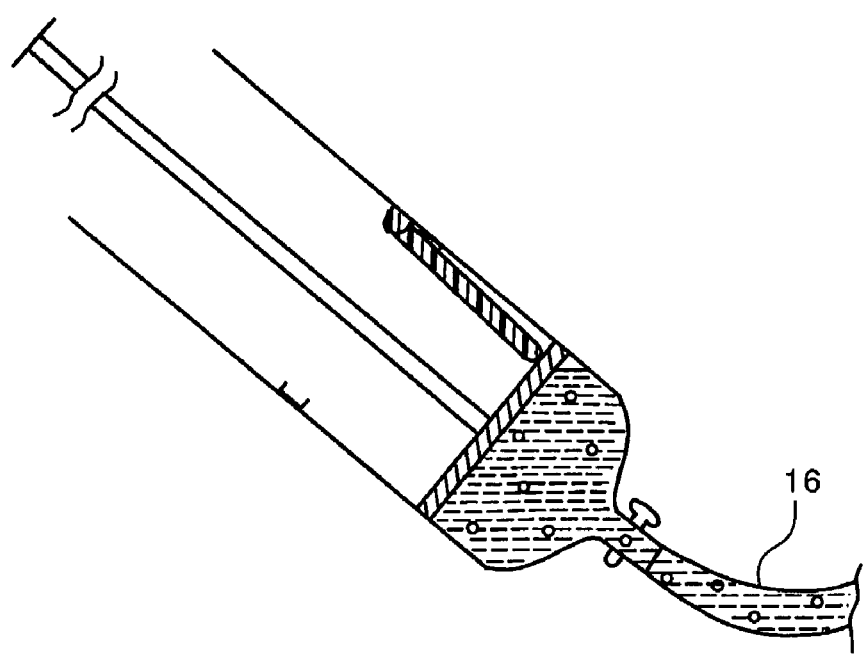
FIG. 1E illustrates delivery of a mixture through a catheter using the syringe of FIG. 1A.

Referring to FIG. 1E, the stopcock 10 is opened to allow the mixed embolic composition 15 to pass via the connector 9, through a catheter 16 for injection into the body (not shown). The plunger can be further lowered to apply pressure for injecting the mixture into the body. In other embodiments, the stopcock 10 can be eliminated where the flow resistance of the syringe outlet and any attached delivery apparatus, such as a catheter, is sufficient to retard flow of solution in response to the pressure in the syringe after rupturing the membrane. The plunger base 11, particularly its circumference, may be made of a flexible rubbery material, such as an elastomeric polymeric material, that can deflect or bend when it engages the membrane so that the plunger can be lowered beyond the membrane into the lower compartment for injection of the mixture into the body.

Figure 2:
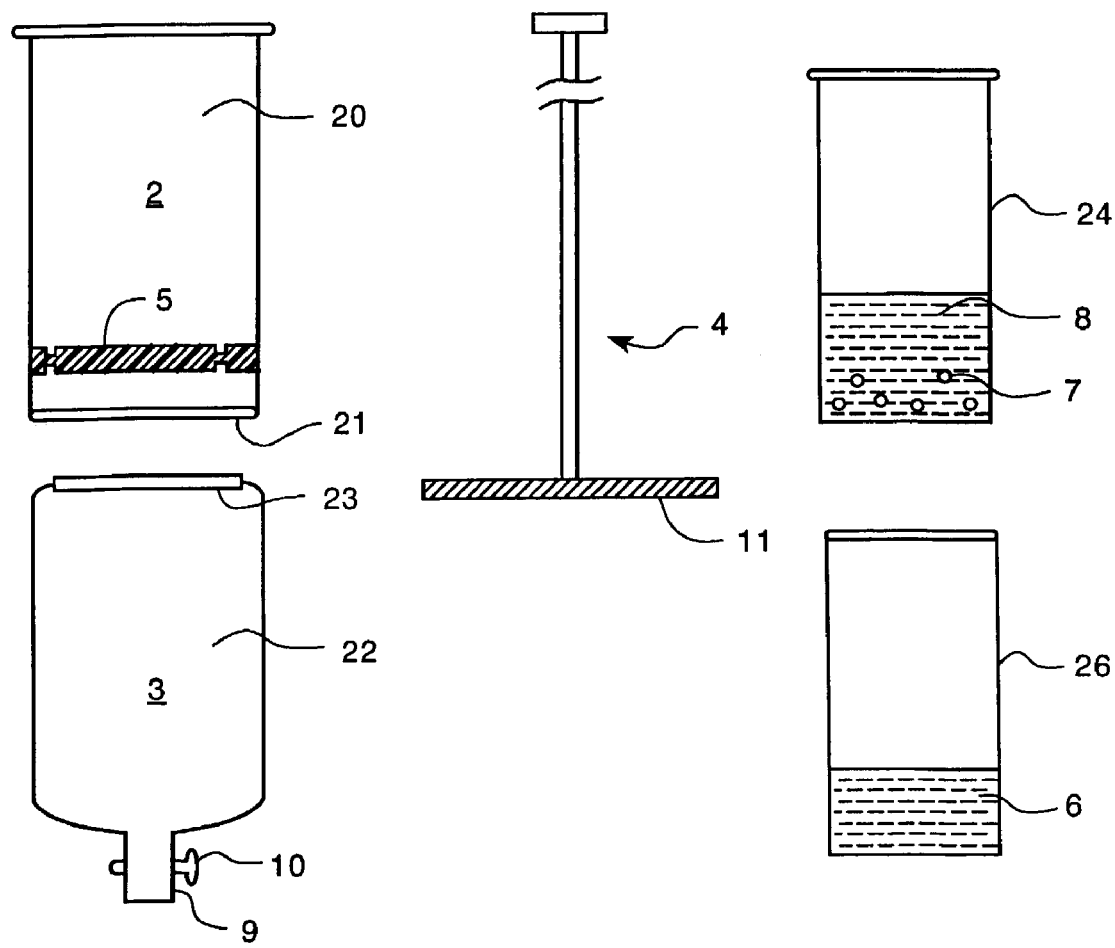
FIG. 2 is a schematic of a kit for mixing and delivery of a composition.

Referring to FIG. 2, a syringe kit is illustrated. The kit includes a syringe barrel made of two detachable sections, 20 and 22, defining the upper compartment 2 and the lower compartment 3, a plunger 4 with a base 11, a vial 24 of embolic material 7 in saline 8, and a vial 26 of contrast agent 6. The upper section 20 of the syringe apparatus has a female-type connector 21 at its bottom end to fit with a male-type connector 23 at the top of the lower section 22. The connection between the upper and lower sections can be, for example, a pressfit, threaded or luer type connection. The lower section 22 has a connector 9 fitted with a stopcock 10. Failure membrane 5 can be placed between the upper and lower sections or can be preattached to one of the sections; in FIG. 2 the membrane is attached to the upper section. For use, the syringe apparatus is assembled as follows: Stopcock 10 is closed and contrast solution 6 from vial 26 is placed in the lower compartment 3 and the upper section is assembled with the lower section. Embolic material 7 along with saline solution 8 is placed in the upper compartment from vial 24. The plunger 4 is then placed in the upper compartment to complete the syringe assembly. The syringe can be provided commercially as a kit with the compartments preloaded with the appropriate components.

Figure 3A:
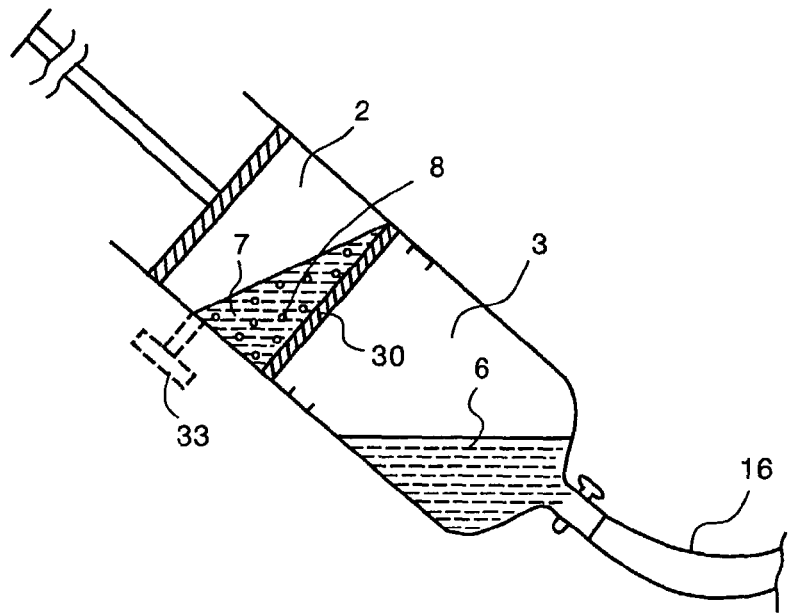
FIG. 3A is a cross-sectional schematic of a syringe apparatus for mixing and delivery of a composition into the body.
Figure 3B:
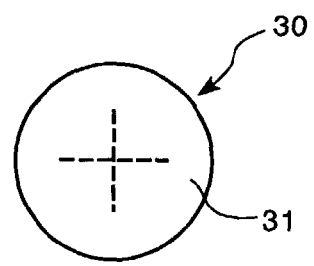
FIG. 3B is a top view of a failure membrane of the syringe of FIG. 3A.
Figure 3C:
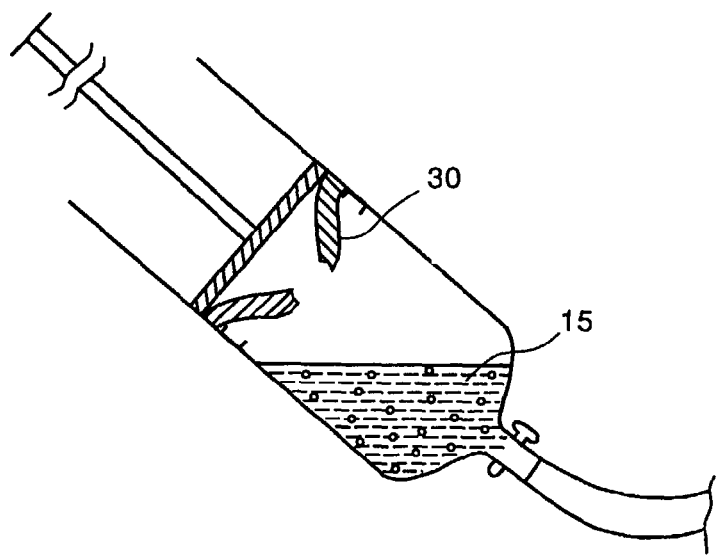
FIGS. 3C and 3D illustrate mixing of the components of a composition using the syringe system of FIG. 3A.
Figure 3D:
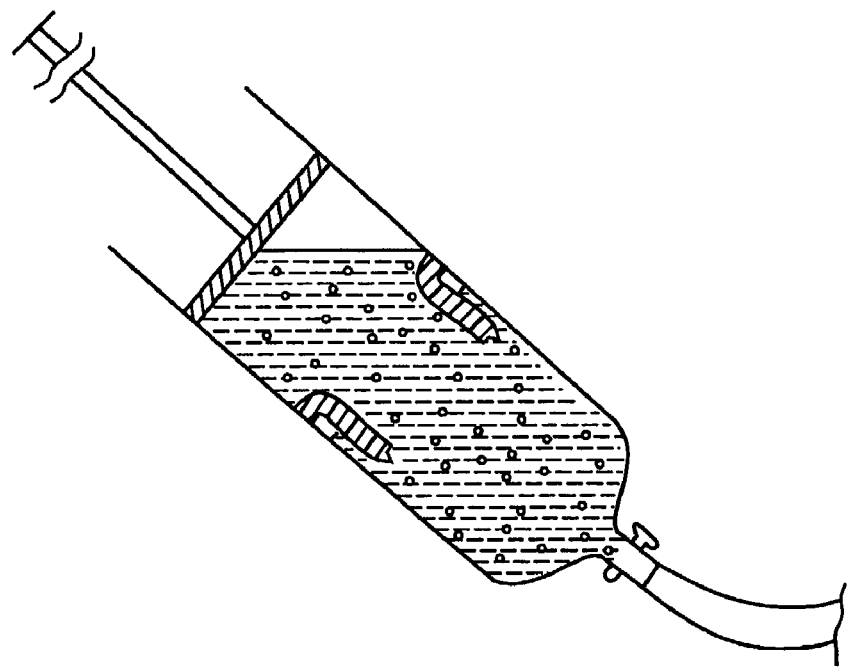
Figure 3E:
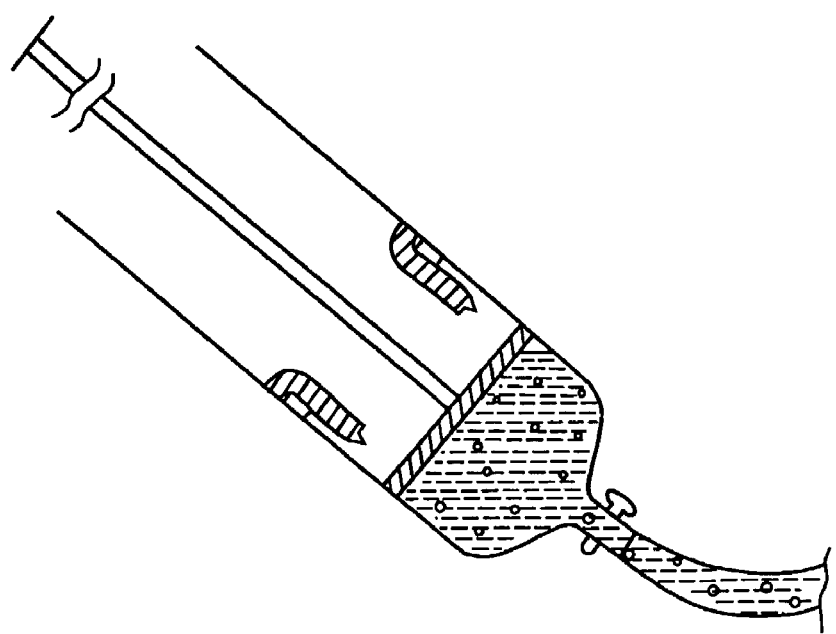
FIG. 3E illustrates delivery of a mixture through a catheter using the syringe of FIG. 3A.

Referring to FIGS. 3A-3E, another embodiment of the syringe apparatus is illustrated. Here the failure membrane 30 is weakened across the center 31, as illustrated in FIG. 3B, for rupture on application of pressure. The rest of the syringe apparatus is as in the first embodiment illustrated in FIG. 1. Referring to FIG. 3C, the stopcock 10 is closed, and when pressure is applied to the upper compartment by depressing the plunger 4, the base 11 of the plunger conveys the applied pressure onto the failure membrane 30 causing its rupture at the weakened regions 31 (to form leaflets). The contents of the upper compartment 2 travel to the lower compartment 3 and mix with it to form the mixed embolic composition 15. Because the embolic particles are initially located in the upper compartment and the contrast in the lower compartment, the particles fall into the contrast solution in a turbulent manner which enhances mixing and the creation of a uniform suspension of the particles in the mixture. Referring to FIG. 3D, the plunger 4 is withdrawn, which causes the embolic composition 15 to backfill the upper compartment. This causes further mixing of the components of the embolic mixture and also prepares the apparatus for delivery of the embolic composition 15. Referring to FIG. 3E, stopcock 10 is opened and the plunger 4 is depressed to allow the embolic composition 15 to pass through the connector 9 to the catheter 16 for injection into the body (not shown). In other embodiments, the upper or lower compartments, or both upper and lower compartments can include a vent valve on the sidewall, (upper vent valve 33 shown in phantom in FIG. 3A) to enable pressure control within the syringe apparatus.

Figure 4A:
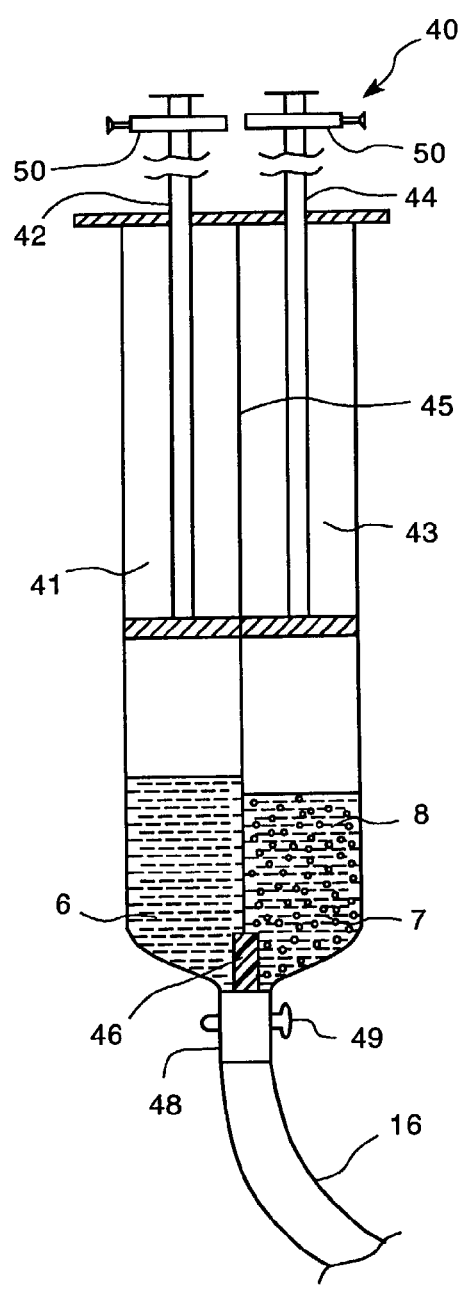
FIG. 4A is a cross-sectional schematic of a syringe apparatus for mixing and delivery of a composition into the body.

Referring to FIG. 4A, in another embodiment, a syringe barrel 40 is provided that has parallel compartments, including a left compartment 41 with a plunger 42, and a right compartment 43, with a plunger 44, both plungers 42 and 44 are fitted with a plunger lock 50. The plunger locks 50 prevent accidental deployment of the plungers. An expanded view of the plunger lock is illustrated in FIG. 4D. The plunger lock 50 includes a frame 54 consisting of a stationary vertical strip 56 placed towards one end of the frame and a movable vertical strip 57 placed towards the other end of the frame, with a threaded hole 58 at the center of the strip 57, through which a screw 59 is passed. The space between the two strips 56 and 57 houses the stem of the plunger. In use, to lock the plunger and prevent its deployment, the strip 57 is moved until the stem of the plunger is tightly held between strips 56 and 57. Counterclockwise movement of the screw 59 further secures the plunger tightly between the two strips 56 and 57. To unlock the plunger for deployment, the screw 59 is turned clockwise and the strip 57 is moved away from the plunger which loosens the grip of the two strips 57 and 58 on the stem of the plunger and unlocks the plunger for deployment. The plunger locks can be made of a metallic or polymeric material. To place the plunger lock 50 on the stem of the plunger, the plunger lock 50 is unlocked, the strip 57 is moved towards the frame, and the lock is slid onto the stem of the plunger from the top and is placed in any desired position on the stem of the plunger.

The compartments are divided by a central divider 45 with a pressure-activated two-way valve 46 at the end of the central divider 45, connecting the two compartments. The pressure-activated valve can include a polymer membrane 47 that can flex into either compartment based on the pressure differential between the compartments. A connector 48, at the bottom of the syringe assembly communicates with both compartments of the syringe and is fitted with a stopcock 49. The left compartment 41 contains the contrast solution 6, and the right compartment 43 contains a mixture of embolic particles 7 and saline solution 8.

Figure 4B:
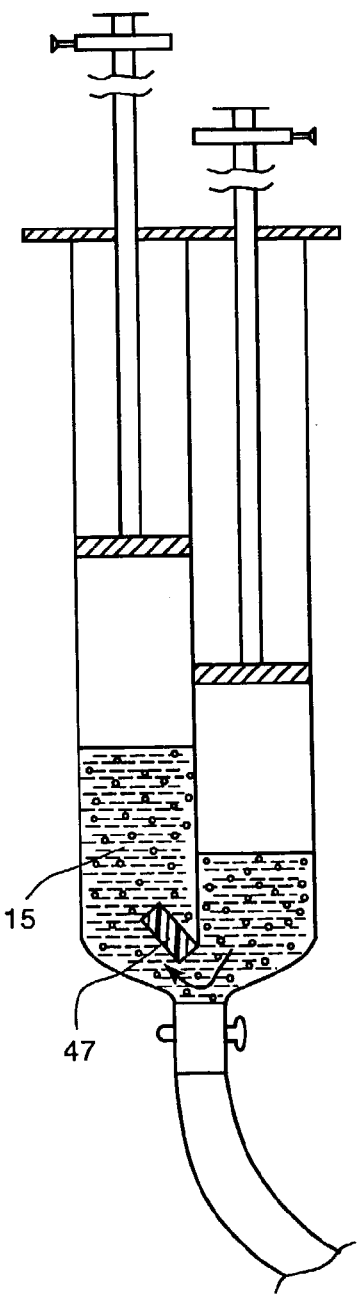
FIG. 4B illustrates mixing of the components of a composition using the syringe of FIG. 4A
Figure 4C:
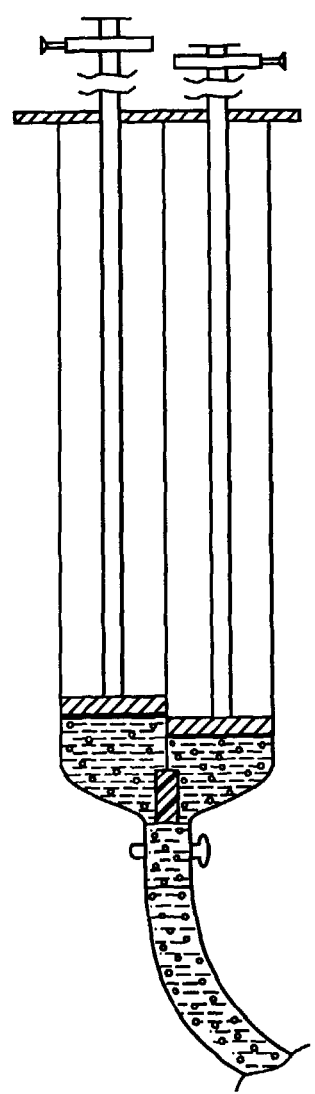
FIG. 4C illustrates delivery of a composition through a catheter using the syringe of FIG. 4A.
Figure 4D:
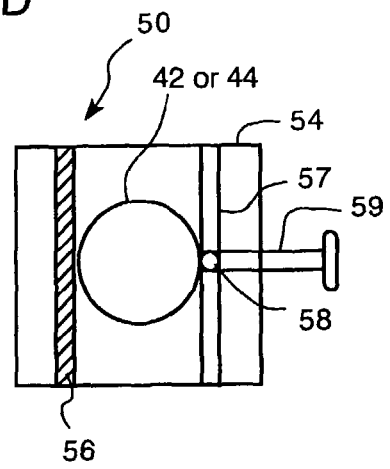
FIG. 4D is a top view of a plunger lock of the syringe of FIG. 4A.

Referring to FIG. 4B, the stopcock 49 is closed, the two plunger locks 50 on the left and right plungers 42 and 44 are unlocked, and the right plunger 44 is lowered causing the membrane 47 to flex into the left compartment and the valve 46 to open. Embolic particles and saline travel to the left compartment (arrow) and mix with the contrast solution to form the embolic mixture 15. Further thorough mixing may be achieved by repeated alternate operation of the two plungers, 42 and 44. Referring to FIG. 4C, the stopcock 49 is opened, the two plungers 42 and 44 are simultaneously depressed such that the embolic mixture 15 passes via the connector 48 through the catheter 16 for injection into the body (not shown). (Alternatively, the plungers can be depressed sequentially.) In other embodiments, the valve membrane can be a failure membrane.

Referring to FIG. 5A and FIG. 5B, another embodiment of the syringe apparatus is illustrated. In this embodiment, there is no two-way valve connecting the two compartments. The central divider 45 extends up to the connector 48 at the bottom of the syringe assembly. Referring to FIG. 5A, the left and right compartments 41 and 43 contain two different sizes of embolic particles, a smaller size 60, and a larger size 62, mixed with saline and/or contrast agent. Referring to FIG. 5B, the left and right compartments 41 and 43 contain two different shapes, a spherical shape 64, and an irregular shape 66, of embolic particles mixed with saline and or contrast agent. The rest of the syringe apparatus is as in the embodiment described in FIG. 4.

The arrangement allows delivery of two different sizes of embolic particles sequentially or simultaneously by sequential or simultaneous operation of the plungers. For example, smaller particles can be delivered first to travel to smaller diameter vessels, followed by larger particles to occlude vessels of larger diameter, upstream of the small diameter vessels. Alternatively, two different shapes of embolic particles can be delivered sequentially (or simultaneously). For example, spherical particles may be delivered first to aggregate and occlude distal regions and the irregular particles may be delivered second for more proximal aggregation.

In use, embolic particles in saline are disposed in the compartments from the top of the syringe, after removing the plungers. Contrast agent is drawn into each compartment from a supply in communication with the connector 48 by releasing the appropriate plunger lock and withdrawing the appropriate plunger. The syringe can be provided commercially as a kit with the compartments preloaded with the appropriate components. For injection into the body, the embolic composition with the desired embolic particle size and shape is injected into the body by release of the appropriate plunger lock, opening the stopcock 49, and depressing the appropriate plunger.

The mixing and delivery system discussed above can be used to deliver a number of compositions. Suitable embolic particles are polymer particles. Preferred particles are spherical particles formed of polyvinyl alcohol, as discussed in "Embolization", U.S. Ser. No. 10/215,594, filed Aug. 9, 2002, the entire contents of which is incorporated herein by reference. A suitable contrast agent is Omnipaque 300 (Nycomed, Buckinghamshire, UK). (Omnipaque is an aqueous solution of iohexol, N.N.-Bis (2,3-dihydroxypropyl)-T-[N-(2,3-dihydroxypropyl)-acetamide]-2,4,6-trilodo-isophthalamide; Omnipaque 300 contains 647 mg of iohexol equivalent to 300 mg of organic iodine per ml). The syringe system can be used to premix and deliver other agents. For example, the systems can be used for mixing of drug agents, such as anti-cancer agents, with polymer particles as described in U.S. Ser. No. 10/232,265, filed Aug. 30, 2002. The system can be used to premix compositions without particles. A valve, such as in FIG. 4A can be used instead of the failure membrane in FIG. 1A. A membrane can be used that is not pressure-activated. For example, the membrane can be deflected by a control lever operable from outside of the syringe barrel. In another example, a sharpened member can be located on the plunger head that pierces the membrane.

Still further embodiments are in the following claims.

What is claimed is:

1. A mixing and delivery medical syringe system, comprising:
   a syringe barrel including an upper compartment and a lower compartment;
   wherein the upper compartment and the lower compartment are detachably connectable to each other;
   a failure membrane disposed in the upper compartment;
   wherein the failure membrane is planar and includes:
      a first peripheral region having a first thickness,
      a second region connected to the first peripheral region, the second region having a second thickness less than the first thickness,
      a third region connected to the second region, the third region having a third thickness that is equal to the first thickness,
      a fourth region connected to the third region, the fourth region having a fourth thickness that is less than the first thickness and that is greater than the second thickness, and
      a fifth peripheral region connected to the fourth region, the fifth peripheral region having a fifth thickness that is equal to the first thickness;
   a vial of embolic material disposed in the upper compartment;
   a vial of contrast agent disposed in the lower compartment; and
   a plunger having a base.

2. The system of claim 1, wherein the upper compartment has a female connector on a bottom end thereof.

3. The system of claim 2, wherein the lower compartment has a male connector on a top end thereof, the male connector being configured to connect with the female connector.

4. The system of claim 1, wherein the second region of the failure membrane is a failure region.

5. The system of claim 1, wherein the fourth region of the failure membrane is a hinge region.

6. The system of claim 5, wherein the failure membrane is circular and has a circumference, and wherein the hinge region extends along a short segment of the circumference of the failure membrane.

7. The system of claim 1, wherein the failure membrane includes cellulose acetate.

8. The system of claim 1, wherein the vial of embolic material includes saline.

9. The system of claim 1, further comprising a stopcock attached to the lower compartment.

* * * * *